United States Patent
LaHaye

(10) Patent No.: US 6,497,700 B1
(45) Date of Patent: Dec. 24, 2002

(54) MULTI-FUNCTION SURGICAL INSTRUMENT FOR FACILITATING OPHTHALMIC LASER SURGERY

(76) Inventor: Leon C. LaHaye, 566 Sand Pit Rd., Arnaudville, LA (US) 70512

(*) Notice: Subject to any disclaimer, the term of this patent is extended or adjusted under 35 U.S.C. 154(b) by 0 days.

(21) Appl. No.: 09/894,264

(22) Filed: Jun. 28, 2001

(51) Int. Cl.[7] ............................................... A61B 18/18
(52) U.S. Cl. ................................................. 606/4; 606/5
(58) Field of Search ................................. 606/4–5, 166; 607/88–92; 604/294–298, 300–325

(56) References Cited

U.S. PATENT DOCUMENTS

| | | | | |
|---|---|---|---|---|
| 5,092,863 A | * | 3/1992 | Schanzlin ........................ 606/5 |
| 5,108,412 A | * | 4/1992 | Krumeich et al. ............ 606/166 |
| 5,437,658 A | * | 8/1995 | Muller et al. .................... 606/5 |
| 5,507,741 A | * | 4/1996 | L'Esperance, Jr. .............. 606/5 |
| 5,941,873 A | * | 8/1999 | Korenfeld ........................ 606/1 |
| 5,980,543 A | * | 11/1999 | Carriazo et al. ............. 606/166 |
| 6,344,040 B1 | * | 2/2002 | Juhasz et al. .................... 606/4 |

* cited by examiner

Primary Examiner—Linda C. M. Dvorak
Assistant Examiner—Ahmed Farah
(74) Attorney, Agent, or Firm—Joseph L. Lemoine, Jr.

(57) ABSTRACT

A multi-function surgical instrument for facilitating ophthalmic surgery of the eye by laser means. Included are a lower ring and an upper ring. The lower ring includes a central aperture to capture the limbus and aid in positioning of the eye. Protuberances on the lower surface of the lower ring, application of vacuum between the lower surface of the ring and the eye, or both may be used to more firmly grip the eye. Ports disposed on the upper surface of the lower ring and connected to a vacuum source may be used to control hydration of the surgical field. Attached to and extending above the upper surface of the lower ring is a sterile platform for reposing temporarily removed tissues during the administration of laser pulses to other tissues. The upper ring is disposed above the surgical bed. Ports disposed along the upper ring and connected to a vacuum source may be used to control smoke and splatters resulting from the ablative procedure and create additional airflow to further control hydration of the surgical field.

45 Claims, 2 Drawing Sheets

(Section 1-1)

MULTI-FUNCTION SURGICAL INSTRUMENT FOR FACILITATING OPHTHALMIC LASER SURGERY

FIELD OF THE INVENTION

In the field of ophthalmic surgery the use of lasers is well known. In laser assisted in-situ kerotomileusis pulses of laser light are used to ablate desired portions of the stromal bed following temporary removal of the outer tissues of the cornea. After replacement of the temporarily removed tissues the cornea is reshaped. During such procedure, and other ophthalmic procedures involving ablation of eye tissue, positioning and fixation of the eye against movement is important, as is proper tissue hydration, control of smoke and splatter, maintaining cleanliness of open tissues, etc. The invention disclosed and claimed herein relates to a multi-function instrument placed on the surface of the eye during ablative eye surgery to assist the ophthalmic surgeon perform laser ablative eye surgery.

BACKGROUND OF THE INVENTION

In corneal surgery the use of lasers is well known. In such procedures precisely controlled pulses of laser light are used to remove thin layers of tissue by ablation. For instance, in photorefractive keratectomy ("PRK") the cornea is reshaped by first removing the epithelium and Bowman's layer (by various means) and ablating the stromal bed by laser (after which the epithelium and Bowman's layer are left to re-form by healing). In laser assisted in-situ kerotomileusis ("LASIK") the cornea is reshaped by temporarily removing the outer layers (epithelium, Bowman's layer and a portion of the stromal bed) thereof by sharp instrument, ablating selected areas of the underlying stromal bed by laser and then replacing of the removed tissues. Various other corneal surgery are also performed using a laser to ablatively remove selected eye tissue.

These procedures encounter some common challenges. The eye must be positioned properly, and fixed against movement therefrom, so that the laser pulses are applied, consistently, to only the selected tissues. Ablation of eye tissue creates airborne plumes of smoke and splatter which can cause subsequent laser pulses to be applied non-uniformly and other adverse effects. Ablation of over-lying tissue can result in non-uniform or excess hydration of the underlying tissue which can result in total, partial and possibly non-uniform underdosage. Migration of exterior fluids into the surgical field can not only mask subsequent treatment, but can also increase the risk of infection or other contaminants.

In addition, in LASIK there are issues regarding placement of the temporarily removed tissues during administration of the laser pulses. To facilitate exact replacement of temporarily removed tissues to their original position at the conclusion of the surgery, they are typically not entirely removed at the beginning of the procedure, but rather left attached by a "hinge" of tissue (forming what is commonly called a corneal "flap"). During ablation this "flap" is typically folded over onto the sclera, where it is exposed to eye fluids, debris from ablated tissue, bacteria and other undesirable materials. In such position there is also the risk that excess eye fluids may float the flap into the laser field where it may be damaged. There is also a risk of damage to this sensitive flap during handling to replace it over the stromal bed.

Other art discloses ophthalmic tools which includes some, but not all, of the features of the multifunction tool herein disclosed and claimed. For instance U.S. Pat. No. 5,108,412 to Rosenbaum et al discloses a suction ring for attachment to the sclera in the limbus plane. This apparatus is used to guide a trepan perpendicularly to the limbus plane. In U.S. Pat. No. 5,980,543 to Carriazo et al a similar suction ring is used to guide a microkeratome parallel to the limbus. In neither of these patents is the suction ring used to fix the position of the eye in relation to a laser or structure not attached to the ring. In neither of these patents does the suction ring include a platform for "storage" and replacement of a corneal flap during a surgical procedure. In neither of these patents are other attributes of the invention, such as plume and splatter evacuation means, means for creating flow of dehydrating gas over the aperture of the ring, means for improved irrigation for a surgical field, etc., disclosed.

Likewise U.S. Pat. Nos. 5,941, 873 and 5,971,977 to Korenfeld shows one, but not other, attributes of the invention disclosed and claimed herein. In these patents there is disclosed a device having a ring-shaped tube with a plurality of apertures disposed about the inner circumference thereof, to aid in smoke removal during an ablative procedure of the eye. These patents do not teach any structure for aspirating fluid away from an open stromal bed nor do they teach a sterile platform on which to repose a corneal flap during an ablative procedure of the eye.

The invention disclosed and claimed herein is a multi-function surgical instrument directed to each of the above-mentioned issues. It provides a means for fixing the position of the eye, as may be required, during surgery. It provides a means for controlling hydration of open and/or ablated eye tissue during surgery. It provides a means to aspirate fluids containing ablative debris from the surgical field. It provides a means to prevent potentially contaminated fluids from migrating from outside to the inside of the surgical field.

Also provided is a sterile platform, elevated above potentially contaminating fluids, upon which to repose a corneal flap (and protect it from smoke and splatters) during surgery. The invention disclosed also provides means for removing smoke resulting from ablation of tissue. Thus the invention disclosed and claimed herein is directed not only to more uniform and consistent application of laser pulses (by establishing good fixation of the eye, removing excess hydration and smoke from the surgical field) but better protects open and/or ablated tissue from contaminating debris and/or bacteria.

DESCRIPTION OF THE PREFERRED EMBODIMENT OF THE INVENTION

While the present invention will be described with reference to preferred embodiments, it will be understood by those skilled in the art that various changes may be made and equivalents may be substituted for elements thereof without departing from the scope of the invention. In addition, modifications may be made to adapt a particular situation or material to the teachings of the invention without departing from the essential scope thereof. It is therefore intended that the present invention not be limited to the particular embodiments disclosed herein, but that the invention will include all embodiments (and legal equivalents thereof) falling within the scope of the appended claims.

Figure 1:
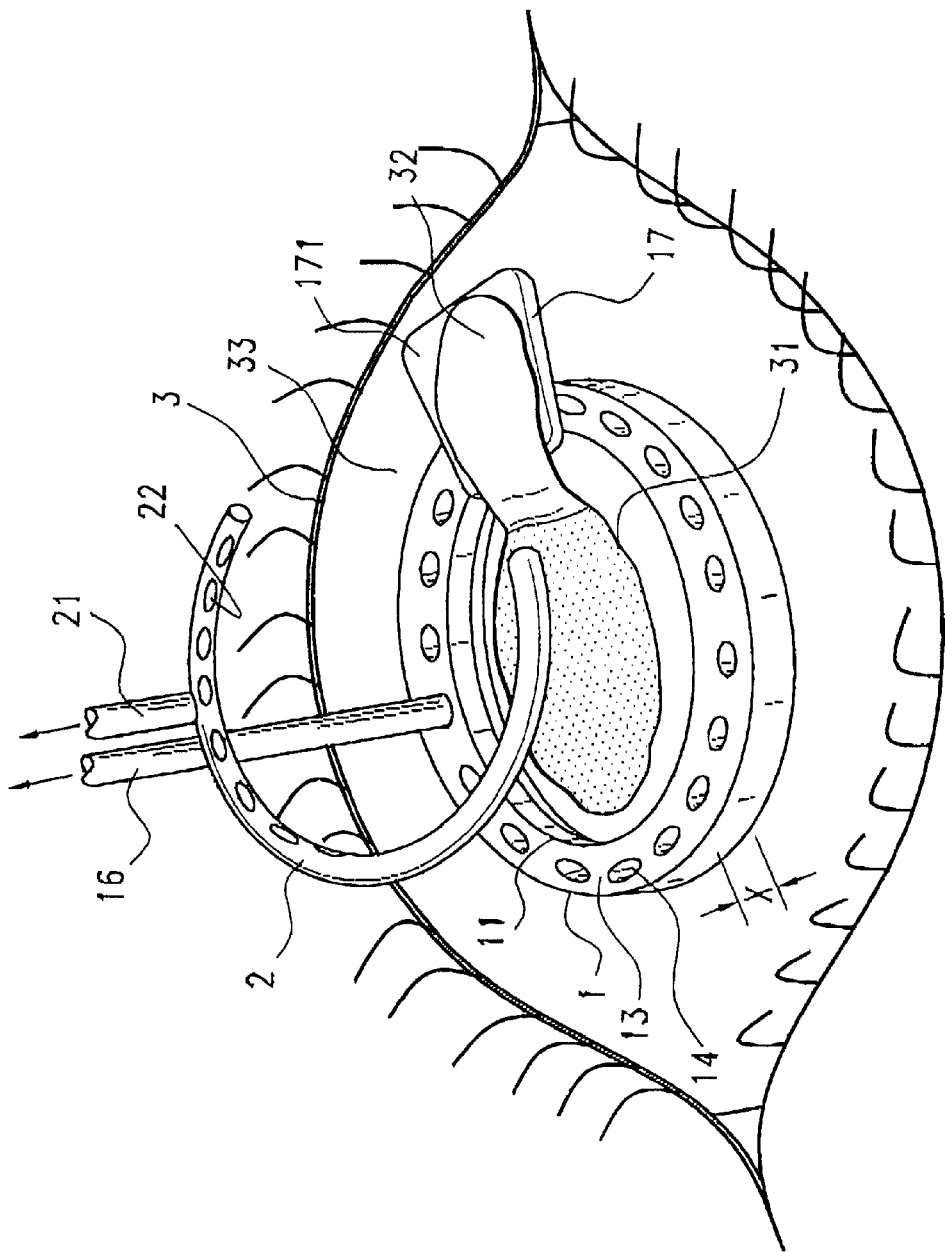
FIG. 1 is a perspective view of the preferred embodiment of the disclosed and claimed invention in the preferred, nasal, position on a patient's eye with an open stromal bed.

FIG. 1 is a schematic view of the preferred embodiment of the surgical instrument of the present invention in position on a human eye 3. Shown are two generally ring-shaped structures, lower ring 1 and upper ring 2, the structure and purpose of which will be herein described in enabling detail.

Figure 2:
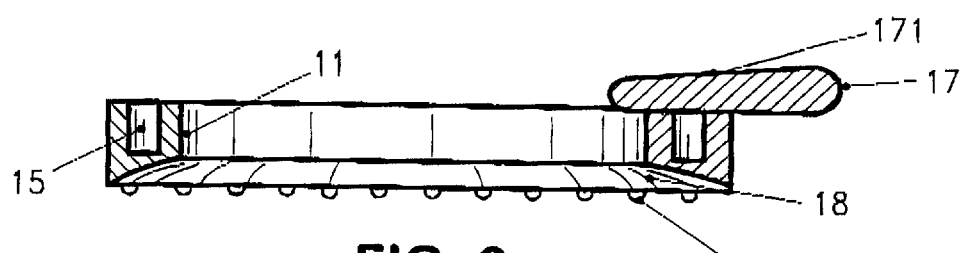
FIG. 2 is a perspective view of the lower surface of the lower ring of an alternative embodiment of the present invention.

Lower ring 1 has several functions. Its central aperture 11 is sized approximately that of the circumference of the limbus, thus "capturing" the corneal bulge of the eye. This tends to fix the position of the eye with respect to the ring. Thus by fixing the position of lower ring 1 the surgeon is able to fix the position of the eye itself. Even more firm fixation of lower ring 1 to the eye may be accomplished by other means, such application of a vacuum between the eye 3 and the lower surface 18 of said ring, or by set of protuberances 19, such as shown in FIG. 2 on the lower surface of said ring. Thus by controlling the position of lower ring 1 the surgeon may firmly fix the position of the eye as he or she may find required.

Figure 3A:
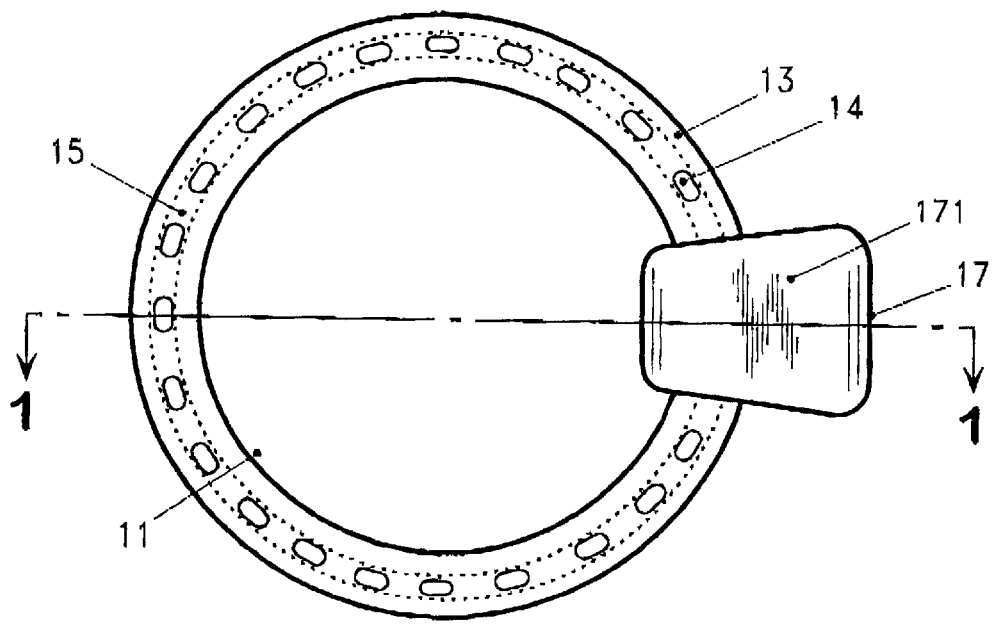
FIG. 3a is an elevational view of the lower ring of the preferred embodiment of the present invention.
Figure 3B:
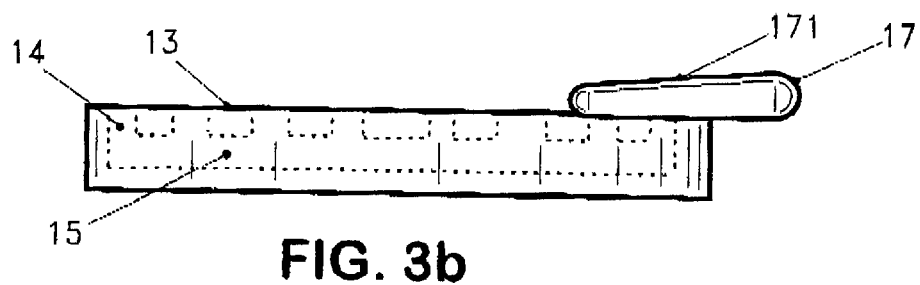
FIG. 3b is a top plan view of the lower ring of the preferred embodiment of the present invention.

Lower ring 1 also provides means to control hydration of the eye tissues which have been opened and/or are being ablated by laser. For example, referring to FIG. 1, in LASIK an open stromal bed 31 is created by removal of corneal flap 32 (by folding said flap onto platform 17). The height of lower ring 1, represented by dimension X, is such that the upper surface 13 of said ring is at, or preferably slightly below, the upper surface of tissues being ablated (which in LASIK will be stromal bed 31); so that excess fluids from or on said tissues tend to flow radially outward and onto upper surface 13 of said ring. The upper surface of said ring may also be inclined radially downward from its inner circumference to aid flow of fluid in a radially outward direction. As said fluids flow onto upper surface 13 of lower ring 1 they will tend to be aspirated into ports 14 disposed in the upper surface 13 of lower ring 1. As is shown in FIG. 3 ports 14 are interconnected by annular passage-way 15 disposed within lower ring 1. Said passage-way is connected to vacuum means by tube 16. In addition to aspirating excess fluids from stromal bed 31, the flow of air into ports 14 tends to create a flow of air over said stromal bed. This passage of air tends to remove excess fluids by evaporation. Thus by controlling the intensity of the vacuum applied to tube 16 the surgeon can control hydration of stromal bed 31. The size of ports 14 may increase in proportion to increased distance from tube 16 so as to cause the flow of air to be more uniform about the circumference of lower ring 1.

The main purpose of platform 17 is to present a sterile area, disposed laterally from stromal bed 31 (thus will not be subject to laser pulses) and elevated above possibly contaminated fluids on sclera 33 upon which to repose the corneal flap 32 (as is shown in FIG. 1) from the time said corneal flap is lifted from stromal bed 31 until re-closed over said bed. Accordingly, as is illustrated in FIG. 1, 2, 3a and 3b, in the preferred embodiment of the invention platform 17 has a generally planar upper surface 171 which is disposed at a height above lower surface 18 of lower ring 1 when lower ring 1 is in position on the eye, extends radially outward from aperture 11 in the direction that the corneal flap 32 to be created during the course of surgery is to be hinged to the eye, and has an area at least the size of said corneal flap 32 (which is usually about 9 to 11 millimeters in diameter).

In the preferred embodiment of the invention, lower ring 1 is also provided with platform 17, which may be permanently or removably attached to upper surface 13 or lower ring 1. This platform not only provides a place to repose the corneal flap 32 (thus keep it off of sclera 33) during application of laser pulses, but also facilitates return of corneal flap 32 to the stromal bed 31 at the conclusion of the surgery. In the preferred embodiment the surfaces of platform 17 are smooth and curved so as to prevent any tearing or sticking of said flap. During application of laser pulses to the stromal bed 31 the corneal flap 32 may be covered with a wet, sterile sponge (not shown) to protect the flap from debris from ablated tissue. In the preferred embodiment the upper surface of platform 17 has a plurality of grooves to facilitate the introduction of fluid between the corneal flap and the platform (thus facilitate "floating" of the flap off of the platform at the conclusion of the surgery).

The primary function of upper ring 2 is smoke removal, but it also enhances air flow over the surgical field to help control excess hydration. In the preferred embodiment upper ring 2 may be a generally circular length of rigid tubing, connected to vacuum means attached to tube 21. Ports 22 extend through the wall of said ring. While other dispositions of ports 22 is comprehended by the invention (such as ports disposed about the outer circumference, at the bottom or top of the tubing) in the preferred embodiment of the invention ports 22 are disposed facing radially inward, on the inner circumference of said tubing. As above, said ports may increase in size in proportion to increased distance from tube 21 in order to produce a more uniform airflow around the ring. Increasing intensity of the vacuum applied to the tube 21 increases air flow and smoke removal.

While upper ring 2 may constitute a full circle (and this embodiment is comprehended by the invention), in the preferred embodiment upper ring 2 does not constitute a full circle, but is only a segment thereof having closed ends, which does not extend above platform 17 (so as to facilitate access to platform 17 by the surgeon).

In most cases upper ring 2 will be disposed approximately 1–3 centimeters above upper surface 13 of lower ring 1. There it may be attached to tube 16 or to a handle or separate frame (not shown) which is also attached to lower ring 1. Upper ring 2 may be attached to a fixed position on any of said structures, or it may be slidably disposed thereon in the direction to and from lower ring 1 (so that the distance between lower ring 1 and upper ring 2 may be varied as circumstances may require). Upper ring 2 may also be made removably attached to any of said structures, so that the surgeon can remove it when desired.

The preferred embodiment of the invention is preferably used with platform 17 disposed nasally, as it is easiest to form the corneal flap 32 with a nasal hinge. But it may be rotatably disposed about the limbus as the particular surgeon may prefer. It will be typically applied to the eye after creation of a corneal flap (typically by microkeratome). After application of the instrument to the eye, the corneal flap will typically be lifted, directly from the stromal bed, onto platform 17, which is sterile. Disposed on platform 17 the corneal flap may be draped with a wet, surgical sponge or other sterile covering to protect it from tissue debris resulting from ablation to follow. Following this, the surgeon will typically apply a desired amount of vacuum to lower ring 1 and upper ring 2, and then use the instrument to fix the position of the eye as required during application of laser pulses. In the simplest form fixing the position of the eye may be by means of the surgeon holding the instrument of the present invention in place with another instrument or by handle attached to the instrument of the present invention, but other forms of positioning mechanisms, including magnetic means, may also be utilized. During the ablative procedure the surgeon may adjust the intensity of vacuum on one or both rings, as he may find effective to control hydration of the stromal bed and remove smoke caused by ablation. At the conclusion of the ablative procedure the stromal bed and other tissues of the eye will typically be thoroughly rinsed to remove ablated tissue and other debris thereon. Typically vacuum will be left on lower ring 1 during rinsing to help remove debris containing fluids from the stromal bed and help prevent debris containing fluid from outside of the surgical field from entering the stromal bed. Following thorough rinsing of the eye (including the corneal flap), the corneal flap will be typically "floated" back into place by application of fluids. Floating of the corneal flap back into place may be accomplished with the instrument of the present invention in place, or as the instrument is lifted from the eye (in which case the instrument itself can be used to guide the flap back over the stromal bed, and is therefore preferred).

It is thus to be appreciated that apparatus in accordance with the principles and teachings of the present inventive disclosure constitutes an advancement in the field of art to which the invention pertains. While the above description contains certain specificities, these should not be construed as limitations on the scope of the invention, but rather as an exemplification of preferred embodiments thereof. Accordingly, the scope of the present invention should be determined not by the embodiments illustrated, but by the appended claims and their legal equivalents.

What is claimed is:

1. A surgical instrument, for placement around the limbus of the eye during corneal surgery by laser, comprising:
   a. a lower ring having a vertical axis, an upper surface and lower surface spaced axially apart and defining a thickness therebetween, and an outer diameter and inner diameter spaced radially apart and defining an annular wall therebetween, all together defining a disc shaped structure having a central aperture surrounded by an annular wall;
   b. wherein the inner diameter of said lower ring is sized to fit closely about the circumference of the limbus of the eye; and,
   c. wherein said lower ring includes a platform having an upper surface which has an area at least the size of a hinged corneal flap to be created in the course of said corneal surgery by laser, which said upper surface extends radially outward from the inner diameter of said lower ring in the direction of the hinge of said corneal flap and is disposed at a height which is above the lower surface of said lower ring where said lower surface of said lower ring intersects with the outer diameter of said lower ring.

2. The surgical instrument of claim 1 wherein said platform has an upper surface which is comprised of a smooth convex curvature.

3. The surgical instrument of claim 2 wherein said smooth convex curvature of said upper surface of said platform includes a plurality of channels which permit the introduction of fluid beneath a corneal flap disposed on the upper surface of said platform.

4. The surgical instrument of claim 3 wherein said lower surface of said lower ring is concavely curved to conform to the curvature of the eye which is outside of the circumference of the limbus thereof.

5. The surgical instrument of claim 4 wherein said concavely curved lower surface of said lower ring further comprises a plurality of convex protuberances for gripping the surface of the eye.

6. The surgical instrument of claim 4 further comprising a port extending from said lower surface of said lower ring to an external vacuum source.

7. The surgical instrument of claim 2 wherein said lower surface of said lower ring is concavely curved to conform to the curvature of the eye which is outside of the circumference of the limbus thereof.

8. The surgical instrument of claim 7 wherein said concavely curved lower surface of said lower ring further comprises a plurality of convex protuberances for gripping the surface of the eye.

9. The surgical instrument of claim 5 further comprising a port extending from said lower surface of said lower ring to an external vacuum source.

10. The surgical instrument of claim 1 wherein said lower surface of said lower ring is concavely curved to conform to the curvature of the eye which is outside of the circumference of the limbus thereof.

11. The surgical instrument of claim 10 wherein said concavely curved lower surface of said lower ring further comprises a plurality of convex protuberances for gripping the surface of the eye.

12. The surgical instrument of claim 10 further comprising a port extending from said lower surface of said lower ring to an external vacuum source.

13. The surgical instrument of claim 1, further comprising:
   d. an upper ring, spaced vertically above said lower ring when said lower ring is positioned on the surface of the eye around the limbus thereof, said upper ring having an internal gas transmissible passage-way, a plurality of gas transmissible ports extending between the exterior surface of said upper ring and said gas transmissible passage-way and a gas transmissible port extending between said gas transmissible passage-way and an external vacuum source.

14. The surgical instrument of claim 13 wherein the plurality of gas transmissible ports extending between the exterior surface of said upper ring are proportionally sized, according to their respective distances from the gas transmissible port extending between said gas transmissible passage-way and an external vacuum source, so as to produce a uniform flow of gases into each of said plurality of gas transmissible ports.

15. The surgical instrument of claim 13 wherein said upper ring is comprised of a circular segment which is open above the platform of the lower ring.

16. The surgical instrument of claim 15 wherein the plurality of gas transmissible ports extending between the exterior surface of said upper ring are proportionally sized, according to their respective distances from the gas transmissible port extending between said gas transmissible passage-way and an external vacuum source, so as to produce a uniform flow of gases into each of said plurality of gas transmissible ports.

17. A surgical instrument, for placement around the limbus of the eye during corneal surgery by laser, comprising:
   a. a lower ring having a vertical axis, an upper surface and lower surface spaced axially apart and defining a thickness therebetween, and an outer diameter and inner diameter spaced radially apart and defining an annular wall therebetween, all together defining a disc shaped structure having a central aperture surrounded by an annular wall;
   b. wherein the inner diameter of said lower ring is sized to fit closely about the circumference of the limbus of the eye;

c. wherein said lower ring includes a platform having an upper surface which has an area at least the size of a hinged corneal flap to be created in the course of said corneal surgery by laser, which said upper surface extends radially outward from the inner diameter of said lower ring in the direction of the hinge of said corneal flap and is disposed at a height which is above the lower surface of said lower ring where said lower surface of said lower ring intersects with the outer diameter of said lower ring;

d. wherein said lower ring includes a fluid transmissible passage-way disposed interiorly of said annular wall along a diameter thereof;

e. wherein said lower ring includes a fluid transmissible port extending between said fluid transmissible passage-way and an external vacuum source; and, f. wherein said lower ring includes a plurality of fluid transmissible ports extending between the upper surface of said lower ring to said fluid transmissible passage-way thereof.

18. The surgical instrument of claim 17 wherein the plurality of fluid transmissible ports extending between the upper surface of said lower ring to said fluid transmissible passage-way thereof are proportionally sized, according to their respective distances from the fluid transmissible port extending between said fluid transmissible passage-way and an external vacuum source, so as to produce a uniform flow of fluids into each of said plurality of fluid transmissible ports.

19. The surgical instrument of claim 17 wherein said thickness of said lower ring is such that when said lower ring is positioned on the surface of the eye around the limbus thereof, the upper surface of said lower ring is disposed below the height of the stromal bed of the eye after creation of a corneal flap thereon.

20. The surgical instrument of claim 17 wherein said platform has an upper surface which is comprised of a smooth convex curvature.

21. The surgical instrument of claim 20 wherein said thickness of said lower ring is such that when said lower ring is positioned on the surface of the eye around the limbus thereof, the upper surface of said lower ring is disposed below the height of the stromal bed of the eye after creation of a corneal flap thereon.

22. The surgical instrument of claim 20 wherein said smooth convex curvature of said upper surface of said platform includes a plurality of channels which permit the introduction of fluid beneath a corneal flap disposed on the upper surface of said platform.

23. The surgical instrument of claim 22 wherein said thickness of said lower ring is such that when said lower ring is positioned on the surface of the eye around the limbus thereof, the upper surface of said lower ring is disposed below the height of the stromal bed of the eye after creation of a corneal flap thereon.

24. The surgical instrument of claim 22 wherein said lower surface of said lower ring is concavely curved to conform to the curvature of the eye which is outside of the circumference of the limbus thereof.

25. The surgical instrument of claim 24 wherein said thickness of said lower ring is such that when said lower ring is positioned on the surface of the eye around the limbus thereof, the upper surface of said lower ring is disposed below the height of the stromal bed of the eye after creation of a corneal flap thereon.

26. The surgical instrument of claim 24 wherein said concavely curved lower surface of said lower ring further comprises a plurality of convex protuberances for gripping the surface of the eye.

27. The surgical instrument of claim 26 wherein said thickness of said lower ring is such that when said lower ring is positioned on the surface of the eye around the limbus thereof, the upper surface of said lower ring is disposed below the height of the stromal bed of the eye after creation of a corneal flap thereon.

28. The surgical instrument of claim 24 further comprising a port extending from said lower surface of said lower ring to an external vacuum source.

29. The surgical instrument of claim 28 wherein said thickness of said lower ring is such that when said lower ring is positioned on the surface of the eye around the limbus thereof, the upper surface of said lower ring is disposed below the height of the stromal bed of the eye after creation of a corneal flap thereon.

30. The surgical instrument of claim 20 wherein said lower surface of said lower ring is concavely curved to conform to the curvature of the eye which is outside of the circumference of the limbus thereof.

31. The surgical instrument of claim 30 wherein said thickness of said lower ring is such that when said lower ring is positioned on the surface of the eye around the limbus thereof, the upper surface of said lower ring is disposed below the height of the stromal bed of the eye after creation of a corneal flap thereon.

32. The surgical instrument of claim 30 wherein said concavely curved lower surface of said lower ring further comprises a plurality of convex protuberances for gripping the surface of the eye.

33. The surgical instrument of claim 32 wherein said thickness of said lower ring is such that when said lower ring is positioned on the surface of the eye around the limbus thereof, the upper surface of said lower ring is disposed below the height of the stromal bed of the eye after creation of a corneal flap thereon.

34. The surgical instrument of claim 30 further comprising a port extending from said lower surface of said lower ring to an external vacuum source.

35. The surgical instrument of claim 34 wherein said thickness of said lower ring is such that when said lower ring is positioned on the surface of the eye around the limbus thereof, the upper surface of said lower ring is disposed below the height of the stromal bed of the eye after creation of a corneal flap thereon.

36. The surgical instrument of claim 17 wherein said lower surface of said lower ring is concavely curved to conform to the curvature of the eye which is outside of the circumference of the limbus thereof.

37. The surgical instrument of claim 36 wherein said thickness of said lower ring is such that when said lower ring is positioned on the surface of the eye around the limbus thereof, the upper surface of said lower ring is disposed below the height of the stromal bed of the eye after creation of a corneal flap thereon.

38. The surgical instrument of claim 36 wherein said concavely curved lower surface of said lower ring further comprises a plurality of convex protuberances for gripping the surface of the eye.

39. The surgical instrument of claim 38 wherein said thickness of said lower ring is such that when said lower ring is positioned on the surface of the eye around the limbus thereof, the upper surface of said lower ring is disposed below the height of the stromal bed of the eye after creation of a corneal flap thereon.

40. The surgical instrument of claim 36 further comprising a port extending from said lower surface of said lower ring to an external vacuum source.

41. The surgical instrument of claim 40 wherein said thickness of said lower ring is such that when said lower ring is positioned on the surface of the eye around the limbus thereof, the upper surface of said lower ring is disposed below the height of the stromal bed of the eye after creation of a corneal flap thereon.

42. The surgical instrument of claim 17, further comprising:

g. an upper ring, spaced vertically above said lower ring when said lower ring is positioned on the surface of the eye around the limbus thereof, said upper ring having an internal gas transmissible passage-way, a plurality of gas transmissible ports extending between the exterior surface of said upper ring and said gas transmissible passage-way and a gas transmissible port extending between said gas transmissible passage-way and an external vacuum source.

43. The surgical instrument of claim 42 wherein the plurality of gas transmissible ports extending between the exterior surface of said upper ring are proportionally sized, according to their respective distances from the gas transmissible port extending between said gas transmissible passage-way and an external vacuum source, so as to produce a uniform flow of gases into each of said plurality of gas transmissible ports.

44. The surgical instrument of claim 42 wherein said upper ring is comprised of a circular segment which is open above the platform of the lower ring.

45. The surgical instrument of claim 44 wherein the plurality of gas transmissible ports extending between the exterior surface of said upper ring are proportionally sized, according to their respective distances from the gas transmissible port extending between said gas transmissible passage-way and an external vacuum source, so as to produce a uniform flow of gases into each of said plurality of gas transmissible ports.

* * * * *